United States Patent [19]

Becker

[11] Patent Number: 4,944,749

[45] Date of Patent: Jul. 31, 1990

[54] IMPLANT AND INFLATING CONSTRUCTION

[76] Inventor: Hilton Becker, 301 Dunbar Rd., Palm Beach, Fla. 33408

[21] Appl. No.: 225,634

[22] Filed: Jul. 27, 1988

Related U.S. Application Data

[63] Continuation of Ser. No. 693,890, Jan. 23, 1985, abandoned.

[51] Int. Cl.$^5$ ............................. A61F 2/12; A61F 2/02
[52] U.S. Cl. ............................................. 623/8; 623/11
[58] Field of Search ............................. 623/7, 8, 11, 12

[56] References Cited

U.S. PATENT DOCUMENTS

| | | | |
|---|---|---|---|
| 3,600,718 | 8/1971 | Boone | 3/36 |
| 3,663,968 | 5/1972 | Mohl et al. | 3/36 |
| 3,800,132 | 3/1974 | Postal | 273/65 C |
| 3,852,832 | 12/1974 | McGhon et al. | 623/8 |
| 3,934,274 | 1/1976 | Hartley, Jr. | 623/8 |
| 4,125,117 | 11/1978 | Lee | 3/36 |
| 4,178,643 | 12/1979 | Cox, Jr. | 3/36 |
| 4,240,630 | 12/1980 | Hoffman | 273/65 D |
| 4,253,201 | 3/1981 | Ross et al. | 3/36 |
| 4,263,682 | 4/1981 | Bejarano | 3/36 |
| 4,433,440 | 2/1984 | Cohen | 623/8 |
| 4,643,733 | 2/1987 | Becker | 623/8 |

FOREIGN PATENT DOCUMENTS 2199266 5/1974 France .......................... 3/36

*Primary Examiner*—David J. Isabella
*Attorney, Agent, or Firm*—Bacon & Thomas

[57] ABSTRACT

An implant and inflating valve construction which includes separate inner and outer membranes each having a separate valve. The outer membrane contains a viscous gel and the inner membrane is inflatable by saline through a removable soft filling tube which passes through the valves. The gel helps seal the valves and around the filling tube when it is in place. The filling tube is stretched during insertion and removal.

6 Claims, 3 Drawing Sheets

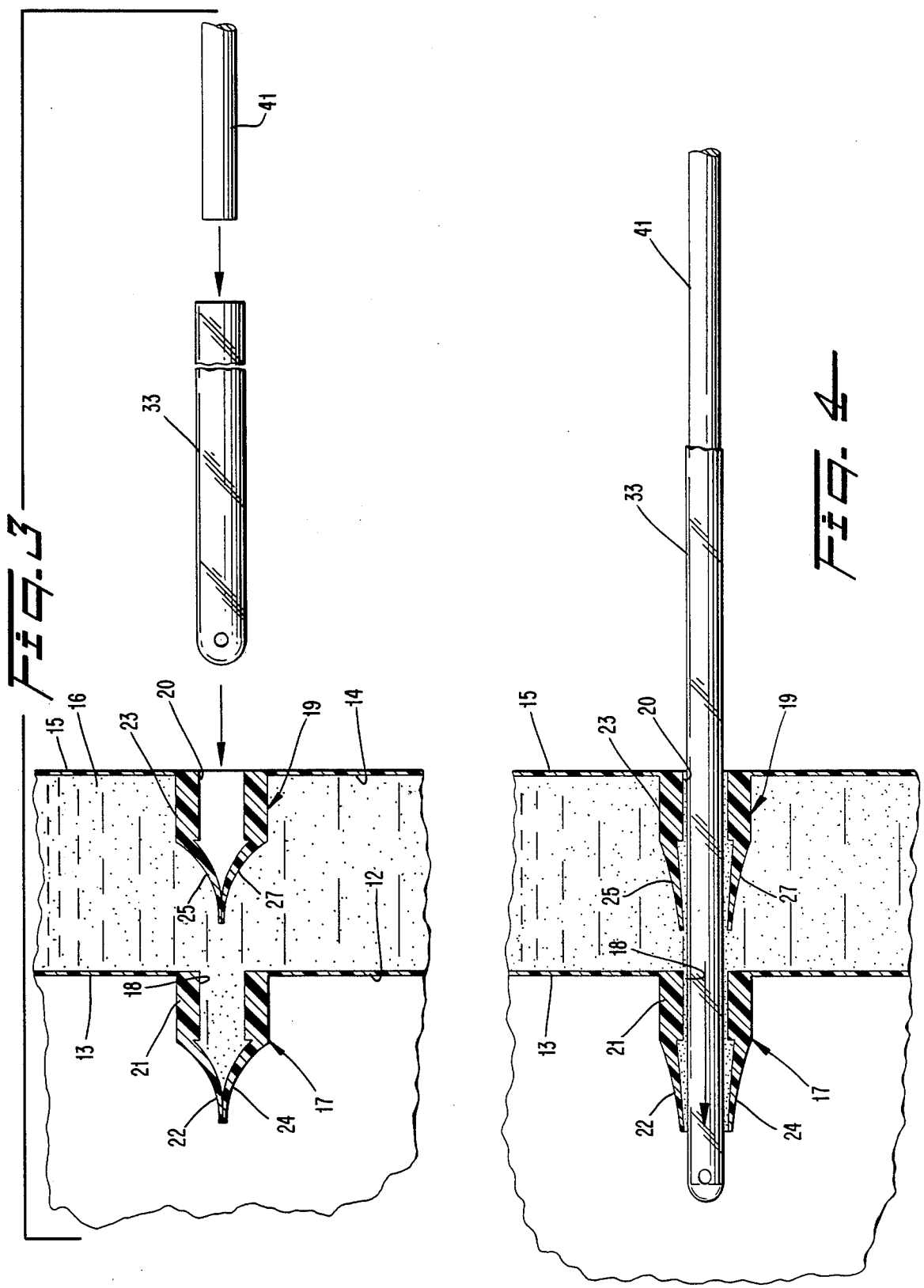

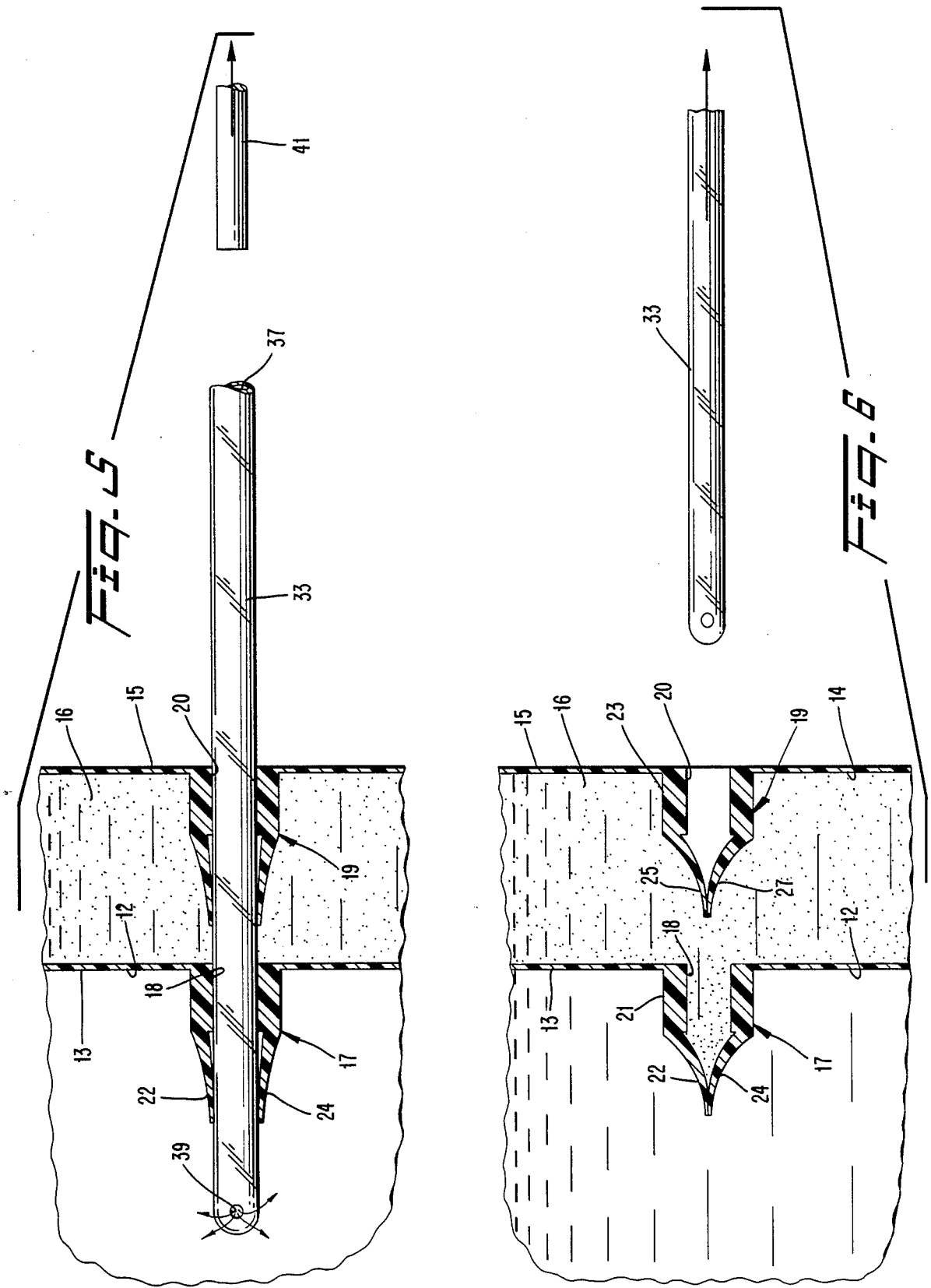

IMPLANT AND INFLATING CONSTRUCTION

This application is a continuation of application Ser. No. 693,890, filed Jan. 23, 1985, now abandoned.

BACKGROUND OF THE INVENTION

The present invention relates to implants, and more particularly to an inflatable implant including separate inner and outer lumens and an improved valve and filling tube construction. The present invention finds particular use in implants used in breast reconstruction and augmentation.

Breast reconstruction often is difficult after a mastectomy because of tight chest wall skin and scarring. It is desirable to expand the skin which allows the surgeon to avoid using skin from other parts of the body. To this end, temporary skin expanders have been used in breast reconstruction, and these are then replaced with a suitably sized, permanent implant. It will be appreciated that this requires two or more surgical procedures.

There are many permanent implants on the market which are useful in breast reconstruction and augmentation. The most commonly used is a single lumen, fixed volume implant utilizing silicone gel. The major drawback in this implant arises from gel bleed which causes capsular contracture. The major advantage is the natural feel which is extremely good.

In an attempt to overcome the "bleed" problem, saline filled implants have been developed. These have greatly reduced the capsule contracture problem, but the feel is not as good. Also, the saline filled implants are subject to spontaneous leakage caused by wave-like motion of the saline which is transmitted to the implant membrane.

There are various "combination" implants, some using a double lumen construction with gel in the inner chamber and saline in the outer chamber, and some with a polyurethane sponge coating to decrease capsule contracture.

A very important goal in implants of this nature is to achieve a natural feel and appearance and to minimize leakage and capsular contracture. Another goal is to facilitate expansion after implantation and to permit volume adjustment.

One implant currently available is that marketed by Cox-Uphoff International termed a Reverse Double Lumen Mammary (RDL$_{TM}$). This is a double membrane, double lumen construction having an outer membrane containing a gel and an inner membrane which is filled with saline. The inner and outer membranes are connected at a retention valve which allows insertion of a rigid filling tube from outside the implant into the inner lumen. By this construction, saline can be injected into the inner lumen at the time of implantation to fill the implant. Upon completion of the filling process and before skin closure, the filling tube is removed. For an explanation and understanding of the retention valve construction described here, reference may be made to U. S. Pat. No. 4,178,643.

The double lumen construction of the CUI implant utilizing silicone gel in the outer lumen and saline in the inner provides a very natural and high quality appearance and feel. However, shear forces arise in this implant at the connected area of the membranes which increases the incidence of leakage. Also, the connected membranes inhibit free movement of the inner and outer membranes relative to each other and detracts from the natural feel and appearance of the implant.

In addition, the filling tube and filling valve constructions in those prior implants which can be filled at the time of surgery are not suitable for inflation or volume adjustment after implantation. A rigid filling tube is required and cannot be left in place for any long period of time because of the danger of puncturing the implant and because of discomfort to the patient caused by the rigid tube. Thus, these implants cannot function as an expander.

It is important that the implant valves be constructed of a soft and pliable material because the valve is a part of the implant and remains in place with the implant. The filling tubes used with these implants often are in place in the valves for some time (in prior devices, before implantation) so that the soft and pliable valve material can become "set" and not recover its original shape when the tube is removed. Still further, such prior valves and filling tubes do not always sealingly cooperate in the desired fashion when the tube is in place. Thus, a relatively high incidence of leakage can result in these implants acting to the detriment of these devices as permanent implants.

SUMMARY OF THE INVENTION

The present invention provides an implant having the desirable characteristics described above. This invention is a combination saline-gel prosthesis which provides a double membrane, double lumen implant wherein an outer membrane forming an outer lumen contains a viscous gel such as a silicone gel, and an inner membrane forming an inner lumen is adapted to be filled with saline for inflation of the implant. The membranes are totally separate from one another and the freedom of movement provided by this construction enhances and maximizes the natural feel and appearance of the implant.

Separate valves are provided in the inner and outer membranes, respectively, and are constructed so that a single, relatively soft and flexible filling tube connected to a reservoir can be used to percutaneously fill the inner lumen over an extended period of time and inflate the implant. The filling tube is sized to have an interference fit with the valves, and means is provided to reduce the cross-sectional dimension of the tube and to stiffen it during insertion. The valves are constructed so that the gel in the outer lumen sealingly cooperates with both valves and with the filling tube when the latter is in place enabling the filling tube to remain in place for an extended period of time. Once the implant is expanded to the desired volume, the filling tube is detached and the prosthesis remains in place as a permanent implant. Upon removal of the filling tube, the valves are prevented from leaking by the sealing action of the gel.

In addition to providing for tissue expansion, the implant allows for volume adjustment post-operatively while the filling tube and reservoir are still connected. Better symmetry of the breasts can be achieved if the implant volume can be adjusted several weeks after surgery when swelling has decreased and the implant has settled into position.

Furthermore, the implant of this invention facilitates a method of tissue expansion which eliminates the fear of pressure on the overlying skin and resulting necrosis from a large implant, so that the patient is reconstructed to the most appropriate breast size.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the implant of this invention comprises inner and outer membranes, the outer membrane containing a viscous gel, first and second valves in the inner and outer membranes, respectively, and adapted to have a singular filling tube passed therethrough for inflating the implant, the gel in the outer membrane sealingly cooperating with the valves and with the filling tube when the latter is in place.

Preferably, the inner and outer membranes are separate and unattached from one another, as are the first and second valves, and the membranes are manually manipulated to align the valves for insertion of the singular filling tube. The inner lumen is filled preferably with saline to inflate the implant, and the valves each comprise separable flaps of soft, pliable material formed integral with the respective membranes and extending inwardly thereof and surrounding openings therein. The filling tube is soft and flexible and is insertable through the valve openings and operable to separate the flaps when passed therebetween, and the flaps are operable to close upon removal of the tube.

In another aspect, the invention is directed to an implant, valve and filling tube construction comprising at least one membrane having an opening therein, the valve including a connecting tube connected to the membrane and surrounding the opening and extending inwardly thereof, the connecting tube having a self-sealing valve means at the inner end thereof, a soft flexible filling tube adapted to be passed through the opening and connecting tube and through the valve means and operable to fill the membrane with a liquid, the filling tube having a larger cross-sectional dimension than the connecting tube, means for applying a longitudinal stretching force to the filling tube reducing its cross-sectional dimension to facilitate its insertion through the connecting tube, the filling tube adapted to return to its original dimension upon removal of the stretching force, whereby to sealingly engage the connecting tube.

Preferably, the filling tube has a longitudinal passage therethrough which is closed at the distal end of the tube and which communicates with a transverse exit passage. The stretching force applying means includes an elongated rod adapted to be inserted through the passage to engage the closed end of the tube. The tube is removed from the valve by pulling which stretches the tube and reduces its cross-section.

In a preferred form, the implant includes concentric inner and outer membranes each having an opening and a valve, and the filling tube is adapted to be passed through both valves to fill the inner membrane. In this form, the outer membrane contains a gel which helps seal both valves when the filling tube is in place and when it is removed.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 3 is an enlarged sectional view of the implant of FIGS. 1 and 2 and showing the filling tube in position for insertion;

FIG. 4 is a view similar to FIG. 3 and showing the filling tube inserted in the implant and longitudinally stretched;

FIG. 5 is a view similar to FIG. 4 and showing the filling tube stretching means removed and the filling tube relaxed; and FIG. 6 is a view similar to FIG. 5 and showing the filling tube detached from the implant.

DESCRIPTION OF THE PREFERRED EMBODIMENT

Reference will now be made in detail to the present preferred embodiment of the invention, an example of which is illustrated in the accompanying drawings.

Figure 1:
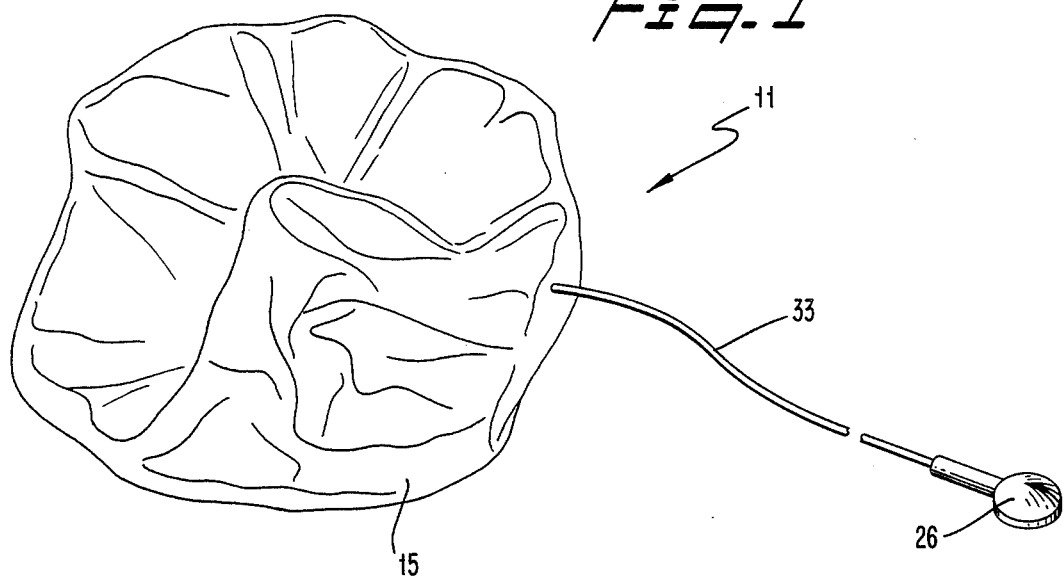
FIG. 1 is a perspective view of an implant constructing according to the present invention shown before inflation and with a filling tube in place.
Figure 2:
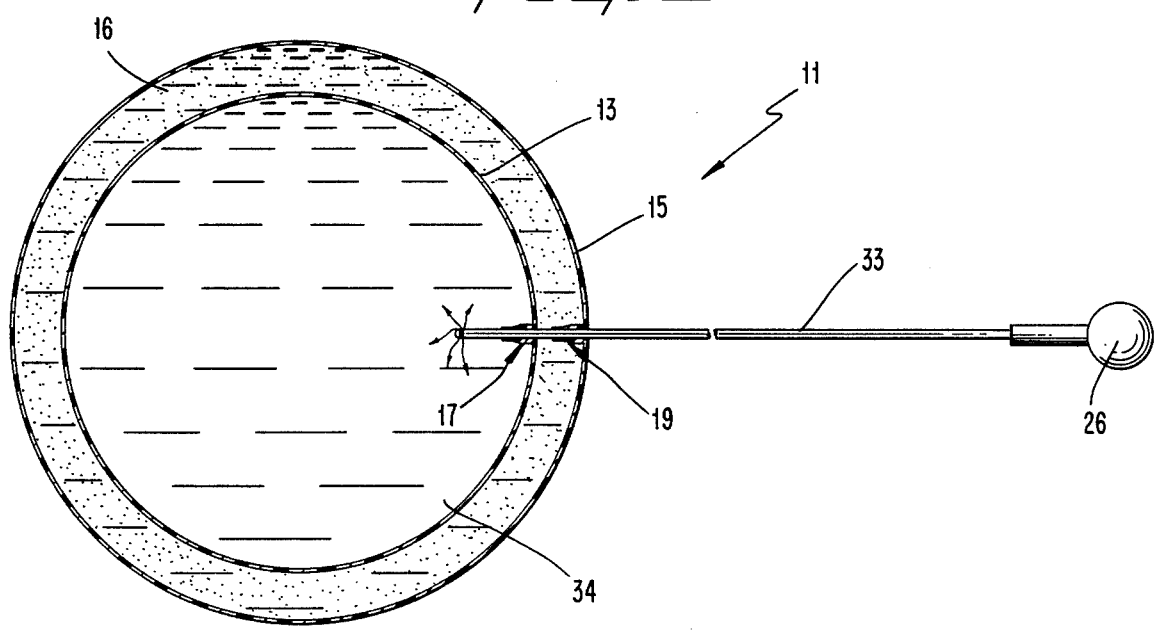
FIG. 2 is a sectional view of the implant of FIG. 1 after inflation.

The preferred embodiment of the implant is shown in FIGS. 1 and 2 and is represented generally by the numeral 11. The implant comprises inner and outer membranes, the outer membrane containing a viscous gel. As embodied herein, the implant 11 includes inner and outer membranes 13, 15 which are generally concentric to one another and form inner and outer concentric lumens 12, 14, respectively (see FIG. 2). The membranes 13, 15 are constructed of a suitable material such as a medical grade silicone rubber which does not react with human tissue, as will be understood by those skilled in the art. The outer membrane 15 contains 25 an amount of viscous gel 16, for example, a silicone rubber gel of medical grade silicone, for purposes to be described.

In accordance with the invention, first and second valves are provided in the inner and outer membranes, respectively. The valves are adapted to have a singular filling tube passed therethrough inflating the implant. As embodied herein and shown in FIG. 2, the inner and outer membranes 13, 15 are provided with valves 17, 19, respectively. The valves include short connecting tubes 21, 23 which surround openings 18, 20 in the membranes 13, 15, respectively, and are formed integral with the membranes and extend inwardly thereof. (See also FIG. 3). A pair of opposed flaps 22, 24 extend inwardly of and surround the tube 21 on the inner membrane 13. In substantially the same fashion, a pair of opposed flaps 25, 27 extend inwardly of and surround the tube 23 on the outer membrane 15.

In accordance with the invention and as further embodied herein, the membranes 13, 15 are separate from and unattached to one another as are the valves 17, 19. The membranes 13, 15 are manually manipulable to align the valves 17, 19 so that a singular filling tube can be passed through the valves for filling the inner membrane and expanding the implant.

A filling tube 33 is shown in place extending through the valves 17, 19 in FIGS. 2 and 5. The filling tube 33 is relatively soft so as not to puncture either of the membranes, and can be inserted as shown at the time the implant 11 is manufactured. Alternatively, a filling tube can be inserted later particularly if one becomes damaged or 25 if it accidentally becomes separated from the implant 11. In either case, the filling tube 33 extends through opening 20, tube 23, and flaps 25, 27 on outer membrane 15, and opening 18, tube 21, and flaps 22, 24 on inner membrane 13. The distal end of tube 33 is connected to a liquid source such as a reservoir 26 and used to fill the inner membrane with a liquid, such as saline 34 and expand the implant over an extended period of time. Upon completion of the filling (and expansion) process, the filling tube 33 is detached from the implant 11 and, in a manner described below, the valves 17, 19 close. For a description of an inflatable permanent implant having a detachable filling tube and reservoir, reference may be made to applicant's copending application Ser. No. 481,912 filed Apr. 4, 1983 now U.S. Pat. No. 4,643,733 which is incorporated herein in its entirety.

As described above, outer membrane 15 contains a silicone gel 16 such as a cohesive silicone rubber gel of medical grade silicone as is used in the Reverse Double Lumen Mammary (RDL$_{TM}$) currently marketed by Cox-Uphoff International of Santa Barbara, Calif. Although the quantity of gel in the outer lumen may vary according to the size of the implant, approximately 40-50 cu. cm. is preferred.

The inner membrane 13 is void prior to implantation of the implant. A small amount of saline (approximately 10% to 20% of its maximum recommended inflation amount) is inflated after implantation to expand the implant to the desired size by delivery of a corresponding quantity of saline 34 thereto. Saline is delivered to the inner membrane 13 by means of the filling tube 33 which, because of its relatively soft and flexible nature, can remain in place for a long period of time after implantation. This allows the implant to be expanded by percutaneous injections into the reservoir over an extended period of time after surgery and provides for volume adjustment of the implant. Once the desired size is achieved, the filling tube 33 is detached. The entire interior contents of the expanded implant 11, i.e., the saline 34 and the gel 16, are under pressure so that flaps 22, 24 and 25, 27 are caused to close thereby sealing the valves 17, 19.

It will be appreciated that once the filling tube 33 is removed, the membranes 13, 15 are totally free to move relative to one another so that the implant 11 is free of any shear forces which otherwise would be present at a connection point between the membranes. This adds to the natural feel and appearance of the implant. The gel in the outer membrane 15 lubricates both membranes and provides the desirable characteristics of a natural breast formation including softness and suppleness. The saline-filled inner membrane 13 provides the necessary adjustment for the over-all size of the implant 11 and, in combination with the gel-filled outer membrane, provides the necessary and desirable round contour of the implant.

In accordance with the invention, the gel in the outer membrane sealingly cooperates with the valves and with the filling tube when the latter is in place. As embodied herein and shown in FIGS. 2 and 5, the connecting tubes 21, 23 are sized to snugly receive the filling tube 33. The flaps 22, 24 and 25, 27 are formed and interconnected with tubes 21, 23 in a manner which produces a biasing force causing flaps 22, 24 to engage and flaps 25, 27 to engage when filling tube 33 is withdrawn.

In actual practice, the filling tube 33 may remain in place in the valves 17, 19 for a long period of time, sometimes for several weeks. In that case, the flaps 22, 24 and 25, 27 may become "set" so that upon removal of the filling tube 33, the flaps may not close fully in spite of the biasing force and the pressure assistance of the saline and gel. In that case, the gel 16 in the outer membrane 15 fills any gap between the flaps 25, 27 which are located in the gel containing outer lumen 14. With the filling tube 33 removed, gel 16 can flow into the short tube 21 on the inner membrane 13 to fill any gap between flaps 22, 24. Thus, the gel 16 effects a proper seal at both valves 15, 17.

As described above, the filling tube 33 preferably is relatively soft and flexible to minimize the likelihood of damage to or puncturing of the membranes 13, 15 and to prevent discomfort to the patient. The short connecting tubes 21, 23 preferably are somewhat stiffer than the filling tube 33. Desirably, a snug fit exists between the filling tube 33 and the connecting tubes 21, 23 and provides an effective seal therebetween as well as to help retain the tube 33 in place. Nevertheless, some crevices or gaps can exist between the filling tube 33 and the connecting tubes 21, 23 which can result in leakage past the valves 15, 17 while the filling tube 33 is in place.

Furthermore, the membranes 13, 15 and the filling tube 33 stretch to an extent as membrane 13 is filled with saline. This may cause some distortion of the connecting tubes 21, 23 which may add to or create crevices or spaces between the filling tube and the connecting tubes 21, 23.

In accordance with the invention and as embodied herein, gel 16 in the outer lumen coats the filling tube 33 during insertion and seeks out and fills any crevices or spaces between the filling tube 33 and the connecting tubes 21, 23 of valves 15, 17 when the filling tube 33 is in place. Thus, the gel 16 sealingly cooperates with the valves 15, 17 and with the filling tube and valves when the filling tube is in place.

In accordance with the invention, means is provided to reduce the cross-sectional dimension of the filling tube during insertion through the membrane valves, and to allow the filling tube to expand after insertion into snug engagement with the connecting tubes.

As embodied herein, the filling tube 33 is sized to provide an interference fit with the connecting tubes 21, 23. The filling tube 33 has an elongated passage 37 therethrough which is closed at the distal end of the tube and which communicates with a transverse exit passage 39. When the filling tube is in place in the implant 11, as shown in FIG. 5, saline from the reservoir 26 flows through passage 37 and exits passage 39 and enters the inner lumen 12.

To facilitate insertion of the soft, flexible filling tube 33 into the implant valves 15, 17, a rigid rod or wire 41 is inserted through the tube passage 37 and, by applying force against the closed end of tube 33, causes it to stretch longitudinally. This reduces the cross-sectional dimension of the filling tube 33, at the same time stiffening it, so that the filling tube 33 is easily inserted through the connecting tubes 21, 23 of valves 15, 17 (see FIG. 4). When insertion is complete, the wire or rod 41 is withdrawn and the filling tube 33 returns to its normal size and snugly engages the connecting tubes 21, 23 (FIG. 5).

When the filling tube 33 is to be detached, a simple pulling force is applied (FIG. 6). Gel which will have coated the filling tube 33 during insertion helps removal. Also, if the holding force of the connecting tubes 21, 23 resists removal of the filling tube, the pulling force on the tube causes it to stretch and its cross-sectional dimension to reduce, thereby facilitating removal.

In accordance with the invention, the implant valve and filling tube construction described above is useful in an implant comprising at least one membrane in which case a valve including a connecting tube is connected to the membrane and extends inwardly thereof. The connecting tube has self-sealing valve means at its inner end. The filling tube is constructed, inserted through, and detached from the valve as described above.

By the foregoing, there has been disclosed an improved implant, valve and filling tube construction calculated to fulfill the inventive objects set forth above and inherent herein. It will be apparent to those skilled in the art that various additions, substitutions, modifications and omissions can be made to the implant of the present invention without departing from the scope or spirit of the invention. Thus, it is intended that the present invention cover the additions, substitutions, modifications and omissions provided they come within the scope of the appended claims and their equivalents.

What is claimed is:

1. An implant system comprising
   inner and outer inflatable lumens each comprised of a respective membrane, said inner and outer lumens being unattached and freely movable relative to each other,
   each of said membranes having a separate valve for inflating each lumen respectively,
   a separate and removable filling tube adapted for penetrating each of said valves when they are in a predetermined position and aligned;
   a volume of viscous gel between said inner and outer lumen for inflating the outer lumen,
   said valves having self sealing means whereby the filling fluid exerts a biasing force on the valve of the inner lumen which together with the viscous gel closes the valve of the inner lumen when the filling tube is removed and the viscous gel exerts a biasing force on the valve of the outer lumen which sealingly closes the valve of the outer lumen.

2. The implant system in claim 1, said filling tube being soft and flexible, whereby to allow said tube to remain in place without puncturing said implant.

3. The implant system in claim 1 wherein said valves each comprise separable flaps of soft, pliable material formed integrally with and extending inwardly of the respective membranes.

4. The implant system in claim 1, said inner membrane adapted to be filled with saline.

5. The implant system in claim 1 wherein said valves including opposed flaps extending inwardly of the respective membranes and normally cooperatively engaging, said flaps adapted to part upon passage of said filling tube therebetween and wherein said filling tube is sized to provide an interference fit with said valves and includes an elongated passage therethrough which is closed at the distal end of said tube.

6. A method of inflating an implant in the human body, wherein said implant is comprised of a first inflatable lumen and a second inflatable lumen that includes and surrounds said first lumen, wherein each lumen is unattached to the outer and is freely movable relative to the other, and wherein each lumen includes a respective valve for passing an inflating fluid through the respective valve to inflate the respective lumen, each said valve being independent of the other and being movable with its respective lumen, and wherein said second lumen is inflated with a viscous gel to a desired state of inflation with the viscous gel in contact with both of said valves, said method of inflating the implant comprising the steps,
   manipulating said lumens and valves to bring said two valves into alignment with each other along a desired path,
   inserting a filling tube through the valve in said second lumen, through said second lumen, through the valve in said first lumen and into the interior of said first lumen,
   implanting said implant in a human body at a prepared location,
   passing an inflating liquid through said filling tube into said first lumen of the inflated implant to inflate the first lumen to a desired amount,
   withdrawing said filling tube from the first lumen and first valve and from the second valve and second lumen without passing any additional fluid through the filling tube once the withdrawal commences, and
   permitting the gel in said second lumen to continue to contact both of said valves to thereby aid in sealing the respective lumens against leakage of the respective fluid therein.

* * * * *